United States Patent
Winters

(10) Patent No.: US 6,565,534 B1
(45) Date of Patent: May 20, 2003

(54) SITE-SPECIFIC POSTOPERATIVE PAIN RELIEF SYSTEM, KIT, AND METHOD

(76) Inventor: Thomas F. Winters, 2031 Venetian Way, Winter Park, FL (US) 32789

( * ) Notice: Subject to any disclaimer, the term of this patent is extended or adjusted under 35 U.S.C. 154(b) by 62 days.

(21) Appl. No.: 09/652,684

(22) Filed: Aug. 31, 2000

Related U.S. Application Data

(62) Division of application No. 09/329,564, filed on Jun. 10, 1999.

(51) Int. Cl.$^7$ .................................................. A61M 1/00
(52) U.S. Cl. ....................................... 604/151; 604/289
(58) Field of Search .................... 604/67, 289, 151, 604/140, 27, 500, 131, 134; 128/203.12, 227, 204.21; 606/22; 137/157; 417/399; 73/1.74

(56) References Cited

U.S. PATENT DOCUMENTS

| | | | |
|---|---|---|---|
| 3,678,932 A | * 7/1972 | Hudson | 128/227 |
| 4,180,067 A | * 12/1979 | Derlien | 604/131 |
| 4,741,736 A | * 5/1988 | Brown | 604/134 |
| 4,824,434 A | * 4/1989 | Seitz | 604/27 |
| 4,872,483 A | * 10/1989 | Shah | 137/157 |
| 5,135,498 A | * 8/1992 | Kam et al. | 604/140 |
| 5,197,322 A | * 3/1993 | Indravudh | 73/1.74 |
| 5,554,011 A | * 9/1996 | Bales et al. | 417/399 |
| 5,681,285 A | * 10/1997 | Ford et al. | 604/140 |
| 5,766,155 A | * 6/1998 | Hyman et al. | 604/151 |
| 5,967,141 A | * 10/1999 | Heinonen | 128/203.12 |
| 6,027,499 A | * 2/2000 | Johnston et al. | 606/22 |
| 6,071,267 A | * 6/2000 | Zamierowski | 604/289 |
| 6,131,571 A | * 10/2000 | Lampotang et al. | 128/204.21 |
| 6,193,704 B1 | * 2/2001 | Winters | 604/500 |
| 6,200,289 B1 | * 3/2001 | Hochman et al. | 604/67 |

* cited by examiner

*Primary Examiner*—Teresa Walberg
*Assistant Examiner*—Leonid M Fastovsky
(74) *Attorney, Agent, or Firm*—Allen, Dyer, Doppelt, Milbrath & Gilchrist, P.A.

(57) ABSTRACT

A system for delivering an anaesthetic-containing fluid to a desired site in a patient includes a catheter for channeling the fluid into a unitary portal penetrating a body. A pump capable of delivering fluid at a constant flow rate is dimensioned to retain sufficient fluid for at least a one-day delivery and is adapted to permit being affixed to the body to permit portability. A fluid line, such as tubing, transports fluid from the pump to the catheter. A kit further includes an introducer needle dimensioned to permit the catheter to pass therethrough. A method of relieving pain at a surgical site postoperatively over an extended period of time includes the steps of inserting an anaesthetic-containing fluid into a pump interior having a capacity sufficient for at least a two-day delivery. The skin of a patient is punctured with an introducer needle at a desired site adjacent the surgical site, and an epidural-type catheter is passed through the introducer needle, which is then removed, leaving the catheter at the desired site. The catheter connects tubing to the pump interior, and fluid is permitted to flow from the pump to the desired site.

10 Claims, 1 Drawing Sheet

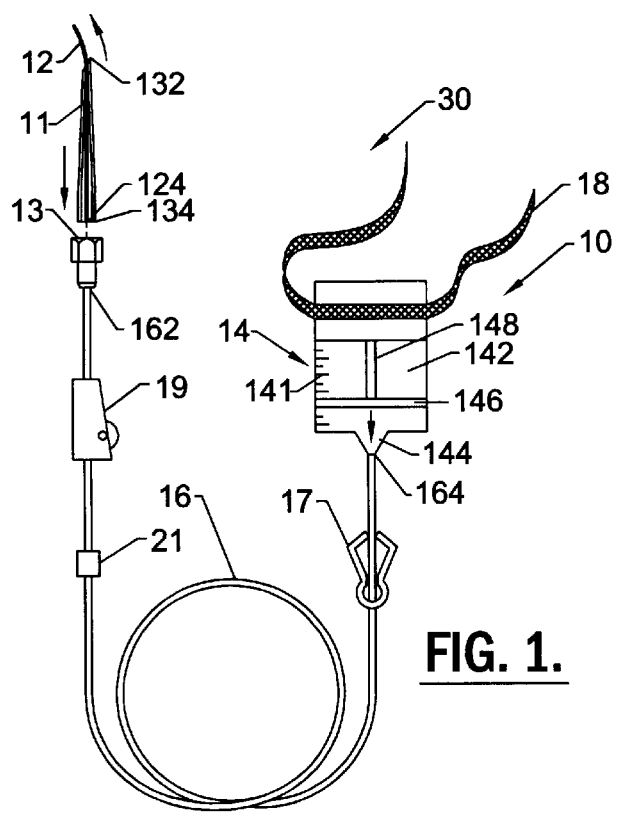
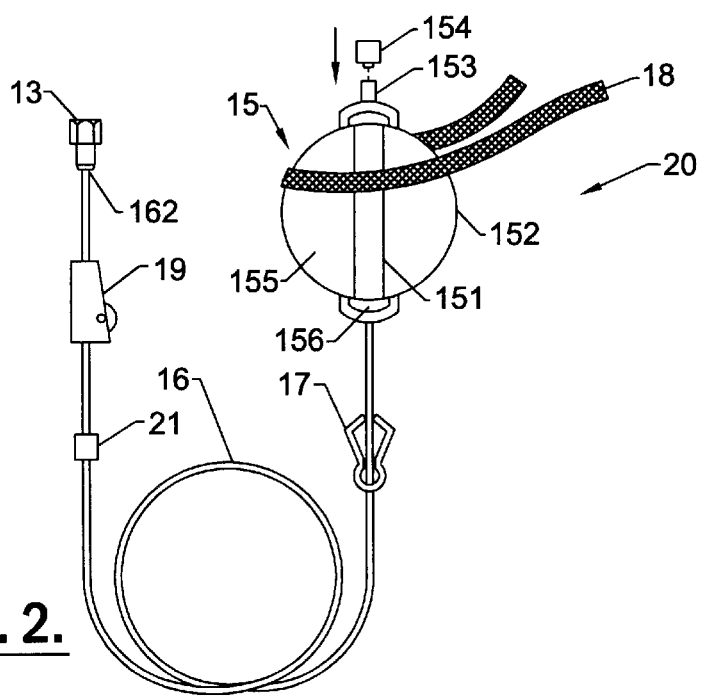
FIG. 1.
FIG. 2.

SITE-SPECIFIC POSTOPERATIVE PAIN RELIEF SYSTEM, KIT, AND METHOD

CROSS REFERENCE TO RELATED APPLICATION

This application is a divisional of and hereby incorporates by reference application Ser. No. 09/329,564, filed Jun. 10, 1999, which is commonly owned and assigned with the present invention.

BACKGROUND OF THE INVENTION

1. Field of the Invention

The present invention relates to systems and methods for providing postoperative pain relief and, more particularly, to such systems and methods for local, site-specific, time-released administration of an anaesthetic.

2. Description of Related Art

Anaesthetic medication is generally required postoperatively for alleviation of discomfort at the surgical site. It has been considered desirable to deliver such medication via a single puncture in order to avoid multiple injections adjacent an area that is already painful.

Two such systems are known to have been disclosed: Reese (U.S. Pat. No. Re. 35,192) teaches a cannula and catheter system that is fed by a spring-loaded syringe wherein the spring has nonlinear characteristics that effect a gradually decreasing delivery rate with spring expansion. LeFevre (U.S. Pat. No. 4,997,420) describes a portable drug delivery device for administering a medication at a constant and self-regulated rate. This device includes a spring-loaded syringe having a reverse-taper cylinder to compensate for the decreasing force exerted by the spring as it expands.

Medication-delivery pumps have been marketed for use in oncological applications to deliver chemotherapeutic agents and for the delivery of antibiotics (the "OutBound" pump, McKinley, Inc., Wheat Ridge, Colo., and others). This pump has a flow-control restrictor and a filter to remove particulates.

In some procedures such as orthopedic operations, a patient can feel very comfortable even immediately after surgery because an anaesthetic will have been delivered into the surgical site, such as a joint. Therefore, until that dose of anaesthetic wears off, the patient experiences less postoperative discomfort. When it does wear off, however, the patient is often dependent upon medication to relieve postoperative pain. Such medication may have side effects and may not alleviate the pain completely, as it is circulated systemically and takes time to reach the target site.

SUMMARY OF THE INVENTION

It is therefore an object of the present invention to provide a portable system for administering a constant infusion of local anaesthetic directly into a desired site.

It is an additional object to provide such a system for postoperative use.

It is a further object to provide a system for delivering a predetermined amount of medication over a predetermined period of time.

It is another object to provide such a system that is portable and permits patient mobility.

A further object is to provide a method for delivering a constant infusion of local anaesthetic into a wound site.

An additional object is to provide a method for alleviating postoperative discomfort.

Another object is to provide a kit for delivering an anaesthetic-containing fluid to a surgical site.

These objects and others are attained by the present invention, a system for delivering an anaesthetic-containing fluid to a desired site in a patient. The system comprises means for channeling an anaesthetic-containing fluid into a unitary portal penetrating a body. The system also includes pump means that has means for creating a constant flow rate. The pump means is dimensioned to retain sufficient fluid for at least a one-day delivery and is adapted to permit being affixed to the body to permit portability. Additionally, a fluid line, such as tubing, transports fluid from the pump means to the channeling means.

A kit further includes an introducer needle dimensioned to permit the channeling means, such as a catheter, to pass therethrough.

A method of relieving pain at a surgical site postoperatively over an extended period of time includes the steps of inserting an anaesthetic-containing fluid into a pump interior having a capacity sufficient for at least a one-day delivery. The skin of a patient is punctured with an introducer needle at a desired site adjacent the surgical site, and an epidural-type catheter is passed through the introducer needle, which is then removed, leaving the catheter at the desired site.

The catheter is connected to tubing, which is also connected in fluid-receiving relation to the pump interior. Then fluid is permitted to flow from the pump to the desired site.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 illustrates a first embodiment of the system of the present invention using a chemotherapy-type pump.

FIG. 2 illustrates a second embodiment of the system using an elastomeric membrane pump.

DETAILED DESCRIPTION OF THE PREFERRED EMBODIMENTS

A description of several preferred embodiments of the present invention will now be presented with reference to FIGS. 1 and 2.

A first embodiment of the anaesthetic delivery system 10 (FIG. 1) comprises a catheter 12 for channeling an anaesthetic-containing fluid into a unitary portal penetrating a body at a desired site adjacent a desired site. Such a site may comprise, for example, a surgical site postoperatively; a trauma site having been treated for a fracture; a joint having been manipulated; or a general surgical site such as a repaired hernia, a resected soft tissue lesion, a laparoscopic or open abdominal procedure, or a mastectomy.

The catheter 12 may comprise, for example, an epidural catheter for subcutaneous insertion, such as, in an exemplary embodiment, a 20-gauge catheter.

The system 10 also comprises a pump 14 having means for creating a constant flow rate and an interior space 142 dimensioned to retain sufficient fluid for at least a 24–72 hour delivery. The pump 14 in this embodiment comprises a portable chemotherapy-type pump, such as the "OutBound®" disposable syringe infuser discussed above (McKinley, Inc., Wheat Ridge, Colo.), although this is not intended as a limitation. Other pumps known in the art are also usable, including, but not limited to, a vacuum- or a spring-driven pump. The pump 14 includes a common inlet/outlet port 144 having means for mating with a syringe for loading and a tubing coupler for delivering fluid, such as a luer lock. A plunger 146 mounted on a movable shaft 148 forces fluid out the port 144. Gradations are provided on the outer wall for visualizing an amount of fluid remaining in the interior space 142.

In an alternate embodiment 20 (FIG. 2) the pump 15 comprises an elastomeric membrane 151 with an exterior bag 152 for holding the fluid. A fill port 153 with a removable cap 154 communicates with the bag's interior 155. An outlet 156 has means for connecting with tubing, such as a luer lock.

A length of tubing 16 serves as a fluid line for transporting fluid from the pump 14,15 to the catheter 12. Along the tubing 16 are positioned, in downstream order from the pump 14,15 to the catheter 12, a clamp 17 for stopping/starting flow, a filter 21, a flow restrictor 19, which is used to control flow rate, and a distal end cap 13. The flow restrictor 19 will, in an exemplary embodiment, permit a flow of 0.5–5.0 ml/h.

In order to permit portability, a strap 18 may be affixable to the pump 14,15. The strap 18 should have sufficient length to permit affixing within tubing's 16 length of the desired site. For example, the pump 14,15 may be desired to be affixed about the thigh following a knee operation.

In another embodiment of the invention, a kit 30 is provided that includes, in addition to the above elements, an introducer needle 11 for puncturing skin at the wound site. The introducer needle 11 has a lumen that is dimensioned to permit the catheter 12 to pass therethrough. An exemplary needle 11, such as for use with the 20-gauge catheter discussed above, comprises a 14- to 18-gauge needle.

In a method of using the system and kit of the present invention, the delivery site, e.g., the patient's joint space, will have already been filled with medication following the surgical procedure. The pump's fill cap, if present, is removed, and an anaesthetic-containing fluid (for example, 100–150 cc of a local anaesthetic such as 0.25–0.5% Bupivicaine HCl, a non-narcotic drug, although this is not intended as a limitation) is inserted into the pump 14, with the tubing's proximal end 164 affixed to the pump's outlet 144 and with the clamp 17 in the clamping configuration. The insertion may be accomplished, for example, with a syringe 21. Following insertion, the fill port cap, if present, is replaced.

The patient's skin is punctured with the introducer needle 11 at a desired site adjacent the surgical site, preferably in a first line through the skin and a second line into the site, in order to avoid leakage out of the catheter 12 following removal. This is accomplished by puncturing the skin, moving the skin and needle 11 together, and then continuing the puncture into the site in a technique known in the art. The needle 11, may comprise, for example, a 14–18 gauge needle, although this is not intended to be a limitation.

A loading dose of local anaesthetic is injected into the surgical site. An epidural-type catheter 12 is passed into the proximal end 134 of the introducer needle 13 until it passes through and exits the distal end 132 thereof into the desired site. Then the introducer needle 13 is removed, and the catheter 12 is taped in place.

The proximal end 124 of the catheter 12 is connected to the tubing's distal end 162. This step typically comprises affixing a luer lock proximal end 124 to the tubing's distal end 162.

Next the flow restrictor 19 is adjusted to a desired flow rate of infusion (e.g., 2 cc/hour, to give up to 48–72 hours of infusion). The clamp 17 is opened, and fluid is permitted to flow to the desired site. The system 10 is secured in place, for example, with tape or the strap 18, and the patient may move about as permitted.

In initial tests, the present systems 10,20 and methods have been shown to provide better postoperative pain control than previously known systems and methods. Among the benefits experienced are a decreased reliance on narcotic administration, earlier return to normal life activities, faster recovery of preoperative range of motion, and decreased need for physical therapy.

A test of 500 orthopedic patients yielded an infection rate of less than 0.2%, with minimal leakage after catheter 12 removal. Patients using the system 10 used an average of 7.6 fewer narcotic pain pills than the norm. Among a subset of knee patients, physical therapy was decreased by an average of 2.2 visits, and the patients were able to return to work an average of 3.6 days sooner.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A site-specific, anaesthetic delivery system comprising:

means for channeling an anaesthetic-containing fluid into a unitary portal penetrating a body, the portal leading to a desired site within the body;

pump means having means for creating a flow rate of fluid therefrom, the pump means dimensioned to retain sufficient fluid for at least a one-day delivery and affixable to the body for permitting portability; and a fluid line for transporting fluid from the pump means to the channeling means.

2. The delivery system recited in claim 1, wherein the pump means comprises a syringe infuser-type pump.

3. The delivery system recited in claim 1, wherein the pump means comprises a vacuum-driven pump.

4. The delivery system recited in claim 1, wherein the pump means comprises a spring-driven pump.

5. A portable kit for providing postsurgical pain relief at a wound site comprising:

a catheter for delivering an anaesthetic-containing fluid adjacent a wound site in a body;

tubing attached to a distal end of the catheter and having a lumen in fluid communication with a lumen of the catheter;

a pump adapted to deliver fluid at essentially constant flow, having at least a two-day fluid capacity, the pump having an outlet in fluid communication with a proximal end of the tubing and an inlet port for filling, the pump affixable to the body for permitting portability; and a flow restrictor having means for adjustably controlling a flow rate through the tubing.

6. The kit recited in claim 5, wherein the pump comprises a chemotherapy delivery-type pump.

7. The kit recited in claim 5, wherein the pump comprises a vacuum-driven pump.

8. The kit recited in claim 5, wherein the pump comprises a spring-driven pump.

9. The system recited in claim 1, further comprising a strap affixable to the pump for permitting pump portability.

10. The kit recited in claim 5, further comprising a strap affixable to the pump for permitting pump portability.

* * * * *